US 9,066,914 B2

(12) United States Patent
Yamasaki et al.

(10) Patent No.: US 9,066,914 B2
(45) Date of Patent: Jun. 30, 2015

(54) PROPHYLACTIC OR AMELIORATING AGENT FOR PIGMENTATION

(75) Inventors: Takashi Yamasaki, Yokohama (JP); Yuko Saitoh, Yokohama (JP); Chihiro Kondo, Yokohama (JP)

(73) Assignee: POLA CHEMICAL INDUSTRIES INC., Shizuoka (JP)

( * ) Notice: Subject to any disclaimer, the term of this patent is extended or adjusted under 35 U.S.C. 154(b) by 0 days.

(21) Appl. No.: 13/521,028

(22) PCT Filed: Jan. 12, 2011

(86) PCT No.: PCT/JP2011/050314
§ 371 (c)(1),
(2), (4) Date: Jul. 6, 2012

(87) PCT Pub. No.: WO2011/087006
PCT Pub. Date: Jul. 21, 2011

(65) Prior Publication Data
US 2012/0282203 A1    Nov. 8, 2012

(30) Foreign Application Priority Data

Jan. 12, 2010  (JP) ................................. 2010-003785

(51) Int. Cl.
| A61K 31/196 | (2006.01) |
| A61K 31/198 | (2006.01) |
| A61K 8/46 | (2006.01) |
| A61K 9/00 | (2006.01) |
| A61K 9/10 | (2006.01) |
| A61Q 19/02 | (2006.01) |
| C07C 309/18 | (2006.01) |

(52) U.S. Cl.
CPC .............. *A61K 31/198* (2013.01); *A61K 8/466* (2013.01); *A61K 9/0014* (2013.01); *A61K 9/10* (2013.01); *A61Q 19/02* (2013.01); *C07C 309/18* (2013.01)

(58) Field of Classification Search
CPC ... A61K 8/466; A61K 9/0014; A61K 31/198; A61K 9/10; C07C 309/18; A61Q 19/02
See application file for complete search history.

(56) References Cited

U.S. PATENT DOCUMENTS

| 6,552,061 | B1 | 4/2003 | Kitazawa et al. |
| 7,375,085 | B1 | 5/2008 | Shiojiri et al. |
| 2002/0058010 | A1 | 5/2002 | Picard-Lesboueyries et al. |
| 2005/0107474 | A1 | 5/2005 | Ungheri et al. |
| 2006/0142382 | A1 | 6/2006 | Morimoto et al. |
| 2011/0245343 | A1* | 10/2011 | Suenobu et al. .............. 514/562 |

FOREIGN PATENT DOCUMENTS

| EA | 009006 B1 | 10/2007 |
| JP | 05-117295 | 5/1993 |
| JP | 11-343235 | 12/1999 |
| JP | 2002-145736 | 5/2002 |
| JP | 2004-323401 | 11/2004 |
| JP | 2005-162699 | 6/2005 |
| JP | 2005-530833 | 10/2005 |
| JP | 2006-052152 | 2/2006 |
| JP | 2008-088113 | 4/2008 |
| JP | 2008-105976 A | 5/2008 |
| WO | WO 00/64926 | 11/2000 |
| WO | WO 01/05369 A1 | 1/2001 |
| WO | WO 2010033733 A1 * | 3/2010 |
| WO | WO 2010/058730 | 5/2010 |

OTHER PUBLICATIONS

Matsushima et al., Journal of Biochemistry (1960), 47, 321-5.*
Takeda, Katsuyuki, "Usefulness of Cosmetics, Evaluation Techniques and future Overview," published by Yakuji Nippo Limited, pp. 149-151, 2001.
International Search Report dated Feb. 15, 2011 issued to priority international application No. PCT/JP2011/050314.
Omori, Takayuki, *Fragrance Journal*, extra (special) issue, No. 14, pp. 118-126, 1995.
Takeda, Katsuhiko, "Usefulness of Cosmetics, Evaluation Techniques and future Overview," published by Yakuji Nippo Limited, pp. 149-151, 2001.
Office Action issued in corresponding Japanese Patent Application No. 2011-549980 on Mar. 11, 2014, with its English translation.
Decision of Grant for Russian Patent Application No. 2012134454, dated Feb. 11, 2015.
Office Action issued in Russian Patent Application No. 2012134454, on Oct. 20, 2014.
Isomerism, URL:http://dic.academic.ru/dic.nsf/bse/89909/Isomeriya, downloaded on Oct. 2, 2014.

* cited by examiner

*Primary Examiner* — Michael G Hartley
*Assistant Examiner* — Robert Cabral
(74) *Attorney, Agent, or Firm* — Knobbe, Martens, Olson & Bear, LLP

(57) ABSTRACT

An object of the present invention is to provide a prophylactic or ameliorating agent for pigmentation having a novel scaffold and an external preparation for skin containing the same as a component. The object is achieved by providing a prophylactic or ameliorating agent for pigmentation comprising a compound represented by the following general formula (1), an isomer thereof, and/or a pharmacologically acceptable salt thereof and an external preparation for skin containing the same as a component:

(1)

$$R_1OOC-CH((CH_2)_n-S(=O)_2-OR_2)-NH-C(=O)-(CH_2)_m-R_3$$

[wherein $R_1$ represents a hydrogen atom or a linear chain or branched alkyl group having 1 to 8 carbon atom(s); $R_2$ represents a hydrogen atom, a substituted or unsubstituted aliphatic hydrocarbon group having 1 to 8 carbon atom(s), a substituted or unsubstituted aromatic group, a substituted or unsubstituted polycyclic fused aromatic group, or a substituted or unsubstituted heterocyclic group having a 5 to 12 carbon atoms; $R_3$ represents a substituted or unsubstituted aromatic group, a substituted or unsubstituted polycyclic fused aromatic group, or a substituted or unsubstituted heterocyclic group having a 5 to 15 carbon atoms; n represents an integer of 1 or 2; and m represents an integer of 0 to 3.]

5 Claims, No Drawings

PROPHYLACTIC OR AMELIORATING AGENT FOR PIGMENTATION

CROSS-REFERENCE TO RELATED APPLICATIONS

This application is the U.S. National Phase under 35 U.S.C. §371 of International Application PCT/JP2011/050314, filed Jan. 12, 2011, which was published in a non-English language, which claims priority to JP Application No. 2010-003785, filed Jan. 12, 2010.

TECHNICAL FIELD

The present invention relates to an external preparation for skin which is preferably usable for cosmetic preparations (including quasi-drugs). In particular, the present invention relates to an external preparation for skin which is characterized to contain a prophylactic or ameliorating agent for pigmentation comprising a compound represented by the following general formula (1), an isomer thereof, and/or a pharmacologically acceptable salt thereof.

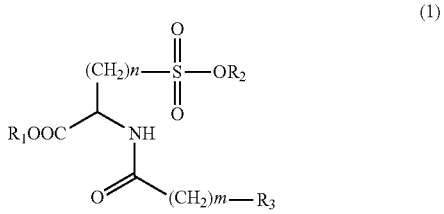

(1)

[wherein $R_1$ represents a hydrogen atom or a linear chain or branched alkyl group having 1 to 8 carbon atom(s), $R_2$ represents a hydrogen atom, a substituted or unsubstituted aliphatic hydrocarbon group having 1 to 8 carbon atom(s), a substituted or unsubstituted aromatic group, a substituted or unsubstituted polycyclic fused aromatic group, or a substituted or unsubstituted heterocyclic group having a 5 to 12 carbon atoms, $R_3$ represents a substituted or unsubstituted aromatic group, a substituted or unsubstituted polycyclic fused aromatic group, or a substituted or unsubstituted heterocyclic group having a 5 to 15 carbon atoms, n represents an integer of 1 or 2, and m represents an integer of 0 to 3.]

BACKGROUND ART

For example, the pigmentation, the freckle, the melasma, and the senile lentigo, which are caused on the skin after the suntan, reside in such a state that the melanin production is extremely facilitated on account of the activation of the pigment cell (melanocyte) in the skin. The component, which is well-known to have the function for preventing or ameliorating the onset and worsening of the skin pigment trouble as described above, is the compound (skin whitening agent) having the skin whitening function including, for example, ascorbic acid derivatives, hydrogen peroxide, colloidal sulfur, glutathione, hydroquinone, and catechol (see, for example, Non-Patent Document 1 and Non-Patent Document 2). External preparations for skin, which are blended with the components as described above as the active ingredients, are widely used. At present, a variety of mechanisms of action have been reported as the mechanism of action possessed by the compound known as the skin whitening agent, including, for example, the tyrosinase enzyme inhibiting action, the tyrosinase-related protein degradation, and the melanin transfer inhibition caused by the suppression of dendrite elongation in melanocyte. Target molecules are present with respect to the respective mechanisms of action. In order to express the high skin whitening effect, an organic low molecular weight compound, which appropriately interacts with the target molecule, is useful. Further, the organic low molecular weight compound, which appropriately interacts with each of the target molecules, has the structural characteristic which differs depending on each of the target molecules. Therefore, studies are vigorously performed as well in relation to the optimization of the chemical structure in order to maximally make the use of the pharmacological action exhibited by the organic low molecular weight compound. At present, studies on the skin whitening agent are not limited to the compound which has the high efficacy and the high selectivity with respect to the existing target molecule, and studies are widened, for example, to the compound which simultaneously acts on a plurality of skin whitening target molecules and the compound which has a novel mechanism of action. The high skin whitening action is expected for the skin whitening agent as described above. Actually, the screening has been carried out in relation to compounds having excellent skin whitening functions while seeking for useful compounds which have various chemical structures or pharmacological characteristics. Any skin whitening agent, which has a novel scaffold, is still demanded even now.

Proteins, which constitute the living body, are composed of 20 types of α-amino acids having different side chains which are called "essential amino acids" in almost all cases. Various biological activities have been reported for α-amino acids described above in addition to the function to constitute the biological components. Further, methionine and cysteine, which are included in α-amino acids described above and each of which has the sulfur atom in the chemical structure, are expected to have any biological activity resulting from the characteristic of the sulfur atom differently from the other α-amino acids, and they are applied to various fields including, for example, pharmaceuticals, cosmetics, and foods. In particular, in the field of the cosmetics, the use has been reported, for example, as a reducing component for hair (see, for example, Patent Document 1) and a moistening component (see, for example, Patent Document 2) in relation to external preparations for skin blended with methionine and cysteine. N-Acetyl-L-cysteine, which is a cysteine derivative, is metabolized into glutathione which is an antioxidant. Therefore, N-acetyl-L-cysteine is used as a supplement. However, when such an α-amino acid derivative, which includes the sulfur atom in the molecular structure, is applied, for example, to a cosmetic preparation, a problem arises, for example, such that the amino acid itself or a composition such as an external preparation for skin are unstable, and an unpleasant smell is caused by decomposition products thereof. On the other hand, it is known that cysteic acid and any derivative having an aliphatic acyl group on its nitrogen atom involve, for example, the oil-soluble base material (see, for example, Patent Document 3), the surfactant (see, for example, Patent Document 4), the mucus dissolving activity, and the antioxidizing function (see, for example, Patent Document 5). Further, it is known that N-benzyl derivative of cysteic acid involves the antioxidizing function (see, for example, Patent Document 6). However, as far as the present inventors know, it is not known that the compound represented by the general formula (1) described above, the isomer thereof, and/or the pharmacologically acceptable salt thereof have/has the prophylactic or ameliorating action for pigmentation. Further, as far as the present inventors know, it has not been known that the concerning compound has the good solubility in the hydrophilic or lipophilic medium, the compound is extremely stable in the forms of the compound and the pharmaceutical preparation, and the compound hardly causes any unpleasant smell when the compound is used into a cosmetic preparation such as an external preparation for skin or the like.

PRECEDING TECHNICAL DOCUMENTS

Patent Documents

Patent Document 1: JP2005-162699A;
Patent Document 2: JP2004-323401A;
Patent Document 3: JP05-117295A;
Patent Document 4: JP2002-145736A;
Patent Document 5: JP2005-530883A;
Patent Document 6: JP11-343235A.

Non-Patent Documents

Non-Patent Document 1: "Usefulness of Cosmetics , Evaluation Techniques and Future Overview", supervised by Katsuyuki TAKEDA, published by YAKUJI NIPPO LIMITED (2001); Non-Patent Document 2: Takayuki Omori, FRAGRANCE JOURNAL, extra (special) issue, No. 14, 1995, 118-126.

SUMMARY OF THE INVENTION

The present invention has been made under the circumstances as described above, an object of which is to provide a prophylactic or ameliorating agent for pigmentation having a novel scaffold which is preferably usable to prevent or ameliorate pigmentation, and an external preparation for skin which contains the same as a component.

Taking the foregoing circumstances into consideration, the present inventors have repeatedly made vigorous efforts while seeking for a novel prophylactic or ameliorating agent for pigmentation preferably usable for a cosmetic preparation (provided that the cosmetic preparation includes quasi-drugs). As a result, it has been found out that the compound represented by the general formula (1) described above, the isomer thereof, and/or the pharmacologically acceptable salt thereof is/are excellent in the prophylactic or ameliorating action for the pigmentation. Thus, the present invention has been completed. The present invention is as follows.

<1> A prophylactic or ameliorating agent for pigmentation, comprising a compound represented by the following general formula (1), an isomer thereof, and/or a pharmacologically acceptable salt thereof:

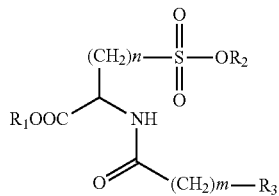

(1)

[wherein:
$R_1$ represents a hydrogen atom or a linear chain or branched alkyl group having 1 to 8 carbon atom(s);

$R_2$ represents a hydrogen atom, a substituted or unsubstituted aliphatic hydrocarbon group having 1 to 8 carbon atom(s), a substituted or unsubstituted aromatic group, a substituted or unsubstituted polycyclic fused aromatic group, or a substituted or unsubstituted heterocyclic group having a 5 to 12 carbon atoms;

$R_3$ represents a substituted or unsubstituted aromatic group, a substituted or unsubstituted polycyclic fused aromatic group, or a substituted or unsubstituted heterocyclic group having a 5 to 15 carbon atoms;

n represents an integer of 1 or 2, and m represents an integer of 0 to 3.]

<2> The prophylactic or ameliorating agent for pigmentation as defined in <1>, wherein in the general formula (1);

$R_1$ represents a hydrogen atom or a linear chain or branched alkyl group having 1 to 8 carbon atom(s);

$R_2$ represents a hydrogen atom;

$R_3$ represents a substituted or unsubstituted aromatic group, a substituted or unsubstituted polycyclic fused aromatic group, or a substituted or unsubstituted heterocyclic group having a 5 to 15 carbon atoms;

n represents an integer of 1 or 2, and m represents an integer of 0 to 3.

<3> The prophylactic or ameliorating agent for pigmentation as defined in <1> or <2>, wherein in the general formula (1);

$R_1$ represents a hydrogen atom or a linear chain or branched alkyl group having 1 to 8 carbon atom(s);

$R_2$ represents a hydrogen atom;

$R_3$ represents a substituted or unsubstituted aromatic group, a substituted or unsubstituted polycyclic fused aromatic group, or a substituted or unsubstituted heterocyclic group having a 5 to 15 carbon atoms;

n represents an integer of 1 or 2, and m represents 0.

<4> The prophylactic or ameliorating agent for pigmentation as defined in any one of <1> to <3>, wherein in the general formula (1);

$R_1$ represents a hydrogen atom or a linear chain or branched alkyl group having 1 to 8 carbon atom(s);

$R_2$ represents a hydrogen atom;

$R_3$ represents a substituted or unsubstituted aromatic group, a substituted or unsubstituted polycyclic fused aromatic group, or a substituted or unsubstituted heterocyclic group having a 5 to 15 carbon atoms;

n represents 1, and m represents 0.

<5> The prophylactic or ameliorating agent for pigmentation as defined in any one of <1> to <3>, wherein the compound represented by the general formula (1) is N-(o-toluoyl) cysteic acid (Compound 1), N-(m-toluoyl)cysteic acid (Compound 2), N-(p-toluoyl)cysteic acid (Compound 3), N-(p-methoxybenzoyl)cysteic acid (Compound 4), N-(4-phenylbenzoyl)cysteic acid (Compound 5), N-(p-toluoyl)homocysteic acid (Compound 6), an isomer thereof, and/or a pharmacologically acceptable salt thereof:

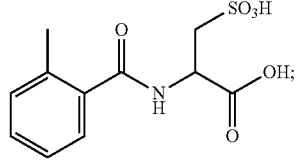

(Compound 1)

N-(o-toluoyl) cysteic acid (Compound 2)

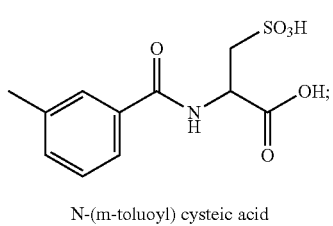

N-(m-toluoyl) cysteic acid (Compound 3)

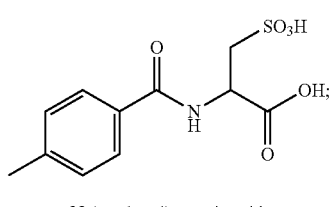

N-(p-toluoyl) cysteic acid (Compound 4)

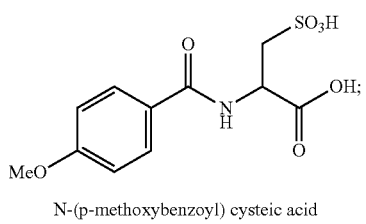

N-(p-methoxybenzoyl) cysteic acid (Compound 5)

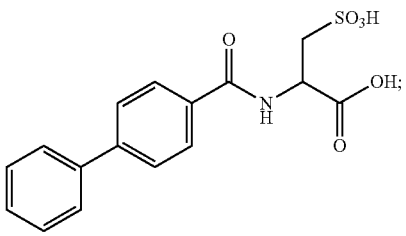

N-(4-phenylbenzoyl) cysteic acid (Compound 6)

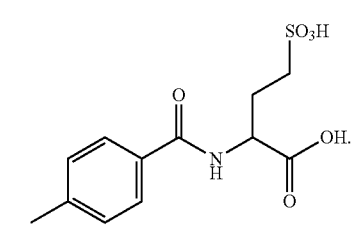

N-(p-toluoyl) homocysteic acid

<6> An external preparation for skin, containing the prophylactic or ameliorating agent for pigmentation as defined in any one of <1> to <5>.

<7> The external preparation for skin as defined in <6>, wherein 0.0001% by mass to 20% by mass of the prophylactic or ameliorating agent for pigmentation is contained with respect to a total amount of the external preparation for skin.

<8> The external preparation for skin as defined in <6> or <7>, wherein the external preparation for skin is a cosmetic preparation (provided that quasi-drug is included).

<9> An external preparation for skin for skin whitening, containing the compound represented by the general formula (1), the isomer thereof, and/or the pharmacologically acceptable salt thereof.

<10> A compound represented by the general formula (1) as defined above, a compound as defined in <2> to <5> defined above, an isomer thereof, and/or a pharmacologically acceptable salt thereof for prophylaxis or amelioration for pigmentation.

<11> A prophylactic or ameliorating method for pigmentation, comprising applying a compound represented by the general formula (1) as defined above, a compound defined in <2> to <5> as defined above, an isomer thereof, and/or a pharmacologically acceptable salt thereof to an object for which prophylaxis or amelioration for pigmentation is required.

MODE FOR CARRYING OUT THE INVENTION

Prophylactic or Ameliorating Agent for Pigmentation as Essential Component in External Preparation for Skin of the Present Invention The external preparation for skin of the present invention is characterized in that the external preparation for skin contains the prophylactic or ameliorating agent for pigmentation comprising the compound represented by the general formula (1) described above, the isomer thereof, and/or the pharmacologically acceptable salt thereof. The effect of the prophylactic or ameliorating agent for pigmentation of the present invention also includes the effect to prevent the pigmentation to be formed in future in addition to the effect to suppress the pigmentation in which the pigmentation, which has been already formed, is thinned or erased. Any component is applicable to the prophylactic or ameliorating agent for pigmentation of the present invention without any special limitation, provided that the component resides in the compound represented by the general formula (1) described above, the isomer thereof, and/or the pharmacologically acceptable salt thereof, and the component has the effect to prevent or ameliorate the pigmentation. However, more preferably, it is possible to appropriately exemplify the component which has the effect to suppress the pigmentation in "Ultraviolet ray-induced pigmentation suppression test using guinea pigs" as described later on. The component, which has the effect to suppress the pigmentation in the pigmentation inhibition test described above, means the component for which the effect to suppress the pigmentation is confirmed in the group to which the substance to be evaluated is administered as compared with the control group (solvent control group). More preferably, it is appropriate to provide the component for which the statistically significant difference is confirmed in the effect to suppress the pigmentation in relation to the group to which the substance to be evaluated is administered as compared with the control group.

The compound represented by the general formula (1), the isomer thereof, and/or the pharmacologically acceptable salt thereof will now be described. In the formula, $R_1$ represents a hydrogen atom or a linear chain or branched alkyl group having 1 to 8 carbon atom(s); $R_2$ represents a hydrogen atom, a substituted or unsubstituted aliphatic hydrocarbon group having 1 to 8 carbon atom(s), a substituted or unsubstituted aromatic group, a substituted or unsubstituted polycyclic fused aromatic group, or a substituted or unsubstituted heterocyclic group having a 5 to 12 carbon atoms; $R_3$ represents a substituted or unsubstituted aromatic group, a substituted or unsubstituted polycyclic fused aromatic group, or a substituted or unsubstituted heterocyclic group having a 5 to 15 carbon atoms; n represents an integer of 1 or 2; and m represents an integer of 0 to 3.

$R_1$ described above represents a hydrogen atom or a linear chain or branched alkyl group having 1 to 8 carbon atom(s), more preferably having 1 to 4 carbon atom(s). Specified examples can be preferably exemplified, for example, by hydrogen atom, methyl group, ethyl group, n-propyl group, isopropyl group, n-butyl group, isobutyl group, sec-butyl group, tert-butyl group, n-pentyl group, isopentyl group, neopentyl group, tert-pentyl group 1-methylbutyl group, n-hexyl group, 1-methylpentyl group, n-heptyl group, and n-octyl group. More preferably, it is possible to appropriately exemplify hydrogen atom, methyl group, and ethyl group.

$R_2$ represents a hydrogen atom, a substituted or unsubstituted aliphatic hydrocarbon group having 1 to 8 carbon atom(s), more preferably having 1 to 4 carbon atom(s), a substituted or unsubstituted aromatic group, a substituted or unsubstituted polycyclic fused aromatic group, or a substituted or unsubstituted heterocyclic group having 5 to 12 carbon atoms. As for the substituent, it is possible to preferably exemplify, for example, an alkyl group having 1 to 6 carbon atom(s), more preferably having 1 to 4 carbon atom(s), an alkoxy group having an alkyl chain having 1 to 6 carbon atom(s), more preferably having 1 to 4 carbon atom(s), an alkoxyalkyl group (preferably composed of an alkoxy group having a alkyl chain having 1 to 4 carbon atom(s) and an alkyl group having 1 to 4 carbon atom(s)), an aromatic or polycyclic fused aromatic group allowed to have an alkyl group having 1 to 4 carbon atom(s) or an alkoxy group having 1 to 4 carbon atom(s) (aromatic group or polycyclic fused aromatic group is preferably phenyl group or naphthyl group), and hydroxy group.

In relation to the group represented by $R_2$, specified examples can be preferably exemplified, for example, by hydrogen atom, methyl group, ethyl group, propyl group, butyl group, pentyl group, hexyl group, heptyl group, octyl group, hydroxyethyl group, hydroxypropyl group, phenyl group, methylphenyl group, ethylphenyl group, propylphenyl group, methoxyphenyl group, ethoxyphenyl group, propyloxyphenyl group, benzyl group, methylbenzyl group, ethylbenzyl group, propylbenzyl group, methoxybenzyl group, ethoxybenzyl group, propyloxybenzyl group, phenylethyl group, methylphenylethyl group, ethylphenylethyl group, propylphenylethyl group, methoxyphenylethyl group, ethoxyphenylethyl group, propyloxyphenylethyl group, naphthyl group, methylnaphthyl group, ethylnaphthyl group, methoxynaphthyl group, ethoxynaphthyl group, naphthylmethyl group, methylnaphthylmethyl group, ethylnaphthylmethyl group, methoxynaphthylmethyl group, methoxynaphthylmethyl group, ethoxynaphthylmethyl group, naphthylethyl group, methylnaphthylethyl group, ethylnaphthylethyl group, methoxynaphthylethyl group, ethoxynaphthylethyl group, and biphenyl group. More preferably, it is possible to appropriately exemplify hydrogen atom, methyl group, ethyl group, and benzyl group.

$R_3$ represents a substituted or unsubstituted aromatic group, a substituted or unsubstituted polycyclic fused aromatic group, or a substituted or unsubstituted heterocyclic group having a 5 to 15 carbon atoms. As for the substituent, it is possible to preferably exemplify, for example, an alkyl group having 1 to 6 carbon atom(s), more preferably having 1 to 4 carbon atom(s), an alkoxy group having an alkyl chain having 1 to 6 carbon atom(s), more preferably having 1 to 4 carbon atom(s), an alkylamino group having an alkyl chain(s) having 1 to 6 carbon atom(s), more preferably having 1 to 4 carbon atom(s), a halogen atom, a halogenated alkyl group (preferably having an alkyl chain having 1 to 4 carbon atom(s)), a hydroxy group, and an amino group.

In relation to the group represented by $R_3$, specified examples can be preferably exemplified, for example, by pyridyl group, methylpyridyl group, ethylpyridyl group, propylpyridyl group, methoxypyridyl group, ethoxypyridyl group, propyloxypyridyl group, hydroxypyridyl group, aminopyridyl group, N-methylaminopyridyl group, N-ethylaminopyridyl group, N,N,-dimethyleminopyridyl group, N,N,-diethylaminopyridyl group, chloropyridyl group, fluoropyridyl group, difluoropyridyl group, trifluoromethylpyridyl group, phenyl group, methylphenyl group, ethylphenyl group, propylphenyl group, methoxyphenyl group, ethoxyphenyl group, propyloxyphenyl group, hydroxyphenyl group, aminophenyl group, N-methylaminophenyl group, N-ethylaminophenyl group, N,N,-dimethylaminophenyl group, N,N-diethylaminophenyl group, chlorophenyl group, fluorophenyl group, difluorophenyl group, trifluoromethylphenyl group, naphthyl group, methylnaphthyl group, ethylnaphthyl group, propylnaphthyl group, methoxynaphthyl group, ethoxynaphthyl group, propyloxynaphthyl group, hydroxynaphthyl group, aminonaphthyl group, N-methylaminonaphthyl group, N-ethylaminonaphthyl group, N,N-dimethylaminonaphthyl group, N,N-diethylaminonaphthyl group, chloronaphthyl group, fluoronaphthyl group, difluoronaphthyl group, trifluoromethylnaphthyl group, biphenyl group, methylbiphenyl group, ethylbiphenyl group, methoxybiphenyl group, and ethoxybiphenyl group. More preferably, it is possible to appropriately exemplify pyridyl group, phenyl group, methylphenyl group, ethylphenyl group, methoxyphenyl group, ethoxyphenyl group, fluorophenyl group, trifluoromethylphenyl group, naphthyl group, and biphenyl group.

The number of the substituent on the aliphatic hydrocarbon group, the aromatic group, the polycyclic fused aromatic group, or the heterocyclic group can be preferably exemplified by 0 to 3, and the number is more preferably 0 or 1. One or more of the substituent(s) as described above can exist independently respectively as the substituent(s) on the aliphatic hydrocarbon group, the aromatic group, the polycyclic fused aromatic group, or the heterocyclic group.

As described above, n represents an integer of 1 or 2, and m represents an integer of 0 to 3.

Those preferably usable as the compound represented by the general formula (1) described above can be preferably exemplified by the compound defined in <2> described above, the isomer thereof, and/or the pharmacologically acceptable salt thereof. Those more preferably usable can be preferably exemplified by the compound defined in <3> described above, the isomer thereof, and/or the pharmacologically acceptable salt thereof. Those much more preferably usable can be preferably exemplified by the compound defined in <4> described above, the isomer thereof, and/or the pharmacologically acceptable salt thereof. Preferred compounds, which are included in the compound represented by the general formula (1) described above and the compounds defined in <2> to <4>, are specifically exemplified by N-(o-toluoyl)cysteic acid (Compound 1), N-(m-toluoyl)cysteic acid (Compound 2), N-(p-toluoyl)cysteic acid (Compound 3), N-(p-methoxybenzoyl)cysteic acid (Compound 4), N-(4-phenylbenzoyl)cysteic acid (Compound 5), N-(p-toluoyl)homocysteic acid (Compound 6), an isomer thereof, and/or a pharmacologically acceptable salt thereof. The compounds as described above have the excellent effect of prophylactic or amelioration for the pigmentation. Further, the compounds are excellent in the solubility in the hydrophilic or lipophilic solvent, and it is easy to produce the pharmaceutical preparation such as the external preparation for skin or the like. Further, the compounds are excellent in the skin retention and the stability in the pharmaceutical preparation, the compounds cause no odor which disturbs the realization of the product, and the compounds exhibit the excellent effect to prevent or ameliorate the pigmentation.

The compound defined in <2> described above will now be described. In the formula, $R_1$ represents a hydrogen atom or a linear chain or branched alkyl group having 1 to 8 carbon atom(s); $R_2$ represents a hydrogen atom; $R_3$ represents a substituted or unsubstituted aromatic group, a substituted or unsubstituted polycyclic fused aromatic group, or a substituted or unsubstituted heterocyclic group having a 5 to 15 carbon atoms; n represents an integer of 1 or 2; and m represents an integer of 0 to 3.

$R_1$ described above represents a hydrogen atom or a linear chain or branched alkyl group having 1 to 8 carbon atom(s). Specified examples can be preferably exemplified, for example, by hydrogen atom, methyl group, ethyl group, propyl group, butyl group, pentyl group, hexyl group, heptyl group, and octyl group. More preferably, it is possible to appropriately exemplify hydrogen atom, methyl group, and ethyl group.

$R_3$ described above represents a substituted or unsubstituted aromatic group, a substituted or unsubstituted polycyclic fused aromatic group, or a substituted or unsubstituted heterocyclic group having a 5 to 15 carbon atoms. As for the substituent, it is possible to preferably exemplify, for example, an alkyl group having 1 to 6 carbon atom(s), more preferably having 1 to 4 carbon atom(s), an alkoxy group having an alkyl chain having 1 to 6 carbon atom(s), more preferably having 1 to 4 carbon atom(s), an alkylamino group having an alkyl chain(s) having 1 to 6 carbon atom(s), more preferably having 1 to 4 carbon atom(s), a halogen atom, a halogenated alkyl group (preferably having an alkyl chain having 1 to 4 carbon atom(s)), a hydroxy group, and an amino group.

In relation to the group represented by $R_3$, specified examples can be preferably described, for example, by pyridyl group, methylpyridyl group, ethylpyridyl group, propylpyridyl group, methoxypyridyl group, ethoxypyridyl group, propyloxypyridyl group, hydroxypyridyl group, aminopyridyl group, N-methylaminopyridyl group, N-ethylaminopyridyl group, N,N,-dimethyleminopyridyl group, N,N,-diethylaminopyridyl group, chloropyridyl group, fluoropyridyl group, difluoropyridyl group, trifluoromethylpyridyl group, phenyl group, methylphenyl group, ethylphenyl group, propylphenyl group, methoxyphenyl group, ethoxyphenyl group, propyloxyphenyl group, hydroxyphenyl group, aminophenyl group, N-methylaminophenyl group, N-ethylaminophenyl group, N,N,-dimethylaminophenyl group, N,N-diethylaminophenyl group, chlorophenyl group, fluorophenyl group, difluorophenyl group, trifluoromethylphenyl group, naphthyl group, methylnaphthyl group, ethylnaphthyl group, propylnaphthyl group, methoxynaphthyl group, ethoxynaphthyl group, propyloxynaphthyl group, hydroxynaphthyl group, aminonaphthyl group, N-methylaminonaphthyl group, N-ethylaminonaphthyl group, N,N-dimethylaminonaphthyl group, N,N-diethylaminonaphthyl group, chloronaphthyl group, fluoronaphthyl group, difluoronaphthyl group, trifluoromethylnaphthyl group, biphenyl group, methylbiphenyl group, ethylbiphenyl group, methoxybiphenyl group, and ethoxybiphenyl group. More preferably, it is possible to appropriately exemplify pyridyl group, phenyl group, methylphenyl group, ethylphenyl group, methoxyphenyl group, ethoxyphenyl group, fluorophenyl group, trifluoromethylphenyl group, naphthyl group, and biphenyl group.

The number of the substituent on the aromatic group, the polycyclic fused aromatic group, or the heterocyclic group can be preferably exemplified by 0 to 3, and the number is more preferably 0 or 1. One or more of the substituent(s) as described above can exist independently respectively as the substituent(s) on the aliphatic hydrocarbon group, the aromatic group, the polycyclic fused aromatic group, or the heterocyclic group.

As described above, n represents an integer of 1 or 2, and m represents an integer of 0 to 3.

The compounds defined in <2> described above, which are not included in the compounds defined in <3> or <4> described above, are specifically exemplified. It is possible to preferably exemplify N-(phenylethylcarbonyl)cysteic acid, N-(phenylpropylcarbonyl)cysteic acid, N-(benzylcarbonyl)cysteic acid, N-(methylbenzylcarbonyl)cysteic acid, N-(ethylbenzylcarbonyl)cysteic acid, N-(propylbenzylcarbonyl)cysteic acid, N-(butylbenzylcarbonyl)cysteic acid, N-(methoxybenzylcarbonyl)cysteic acid, N-(ethoxybenzylcarbonyl)cysteic acid, N-(propyloxybenzylcarbonyl)cysteic acid, N-(butyloxybenzylcarbonyl)cysteic acid, N-(hydroxybenzylcarbonyl)cysteic acid, N-(aminobenzylcarbonyl)cysteic acid, N—(N'-methylaminobenzylcarbonyl)cysteic acid, N—(N'-ethylaminobenzylcarbonyl)cysteic acid, N—(N',N'-dimethylaminobenzylcarbonyl)cysteic acid, N—(N',N'-diethylaminobenzylcarbonyl)cysteic acid, N-(chlolobenzylcarbonyl)cysteic acid, N-(fluorobenzylcarbonyl)cysteic acid, N-(difluorobenzylcarbonyl)cysteic acid, N-(trifluoromethylbenzylcarbonyl)cysteic acid, N-(phenylethylcarbonyl)cysteic acid ethyl ester, N-(phenylpropylcarbonyl)cysteic acid ethyl ester, [N-(benzylcarbonyl)cysteic acid]ethyl ester, [N-(methylbenzylcarbonyl)cysteic acid]ethyl ester, [N-(ethylbenzylcarbonyl)cysteic acid]ethyl ester, [N-(propylbenzylcarbonyl)cysteic acid]ethyl ester, [N-(butylbenzylcarbonyl)cysteic acid]ethyl ester, [N-(methoxybenzylcarbonyl)cysteic acid]ethyl ester, [N-(ethoxybenzylcarbonyl)cysteic acid]ethyl ester, [N-(propyloxybenzylcarbonyl)cysteic acid]ethyl ester, [N-(butyloxybenzylcarbonyl)cysteic acid]ethyl ester, [N-(hydroxybenzylcarbonyl)cysteic acid]ethyl ester, [N-(aminobenzylcarbonyl)cysteic acid]ethyl ester, [N—(N'-methylaminobenzylcarbonyl)cysteic acid]ethyl ester, [N—(N'-ethylaminobenzylcarbonyl)cysteic acid]ethyl ester, [N—(N',N'-dimethylaminobenzylcarbonyl)cysteic acid]ethyl ester, [N—(N',N'-diethylaminobenzylcarbonyl)cysteic acid]ethyl ester, [N-(chlolobenzylcarbonyl)cysteic acid]ethyl ester, [N-(fluorobenzylcarbonyl)cysteic acid]ethyl ester, [N-(difluorobenzylcarbonyl)cysteic acid]ethyl ester, [N-(trifluoromethylbenzylcarbonyl)cysteic acid]ethyl ester, N-(phenylethylcarbonyl)homocysteic acid, N-(phenylpropylcarbonyl)homocysteic acid, N-(benzylcarbonyl)homocysteic acid, N-(methylbenzylcarbonyl)homocysteic acid, N-(ethylbenzylcarbonyl)homocysteic acid, N-(propylbenzylcarbonyl)homocysteic acid, N-(butylbenzylcarbonyl)homocysteic acid, N-(methoxybenzylcarbonyl)homocysteic acid, N-(ethoxybenzylcarbonyl)homocysteic acid, N-(propyloxybenzylcarbonyl)homocysteic acid, N-(butyloxybenzylcarbonyl)homocysteic acid, N-(hydroxybenzylcarbonyl)homocysteic acid, N-(aminobenzylcarbonyl)homocysteic acid, N—(N'-methylaminobenzylcarbonyl)homocysteic acid, N—(N'-ethylaminobenzylcarbonyl)homocysteic acid, N—(N',N'-dimethylaminobenzylcarbonyl)homocysteic acid, N—(N',N'-diethylaminobenzylcarbonyl)homocysteic acid, N-(chlolobenzylcarbonyl)homocysteic acid, N-(fluorobenzylcarbonyl)homocysteic acid, N-(difluorobenzylcarbonyl)homocysteic acid, N-(trifluoromethylbenzylcarbonyl)homocysteic acid, N-(phenylethylcarbonyl)homocysteic acid ethyl ester, N-(phenylpropylcarbonyl)homocysteic acid ethyl ester, [N-(benzylcarbonyl)homocysteic acid]ethyl ester, [N-(methylbenzylcarbonyl)homocysteic acid]ethyl ester, [N-(ethylbenzylcarbonyl)homocysteic acid]ethyl ester, [N-(propylbenzylcarbonyl)homocysteic acid]ethyl ester, [N-(butylbenzylcarbonyl)homocysteic acid]ethyl ester, [N-

(methoxybenzylcarbonyl)homocysteic acid]ethyl ester, [N-(ethoxybenzylcarbonyl)homocysteic acid]ethyl ester, [N-(propyloxybenzylcarbonyl)homocysteic acid]ethyl ester, [N-(butyloxybenzylcarbonyl)homocysteic acid]ethyl ester, [N-(hydroxybenzylcarbonyl)homocysteic acid]ethyl ester, [N-(aminobenzylcarbonyl)homocysteic acid]ethyl ester, [N—(N'-methylaminobenzylcarbonyl)homocysteic acid]ethyl ester, [N—(N'-ethylaminobenzylcarbonyl)homocysteic acid]ethyl ester, [N—(N',N'-dimethylaminobenzylcarbonyl) homo cysteic acid]ethyl ester, [N—(N',N'-diethylaminobenzylcarbonyl)homocysteic acid]ethyl ester, [N-(chlolobenzylcarbonyl)homocysteic acid]ethyl ester, [N-(fluorobenzylcarbonyl)homocysteic acid]ethyl ester, [N-(difluorobenzylcarbonyl)homocysteic acid]ethyl ester, [N-(trifluoromethylbenzylcarbonyl)homocysteic acid]ethyl ester, isomers thereof, and/or pharmacologically acceptable salts thereof.

The compounds as described above have the excellent effect of prophylactic or amelioration for the pigmentation. Further, the compounds are excellent solubility in the hydrophilic or lipophilic solvent, and it is easy to produce the pharmaceutical preparation such as the external preparation for skin or the like. Further, the compounds are excellent skin retention and stability in the preparation, and the compounds exhibit the excellent effect to prevent or ameliorate the pigmentation.

The compound defined in <3> described above will now be described. In the formula, $R_1$ represents a hydrogen atom or a linear chain or branched alkyl group having 1 to 8 carbon atom(s); $R_2$ represents a hydrogen atom; $R_3$ represents a substituted or unsubstituted aromatic group, a substituted or unsubstituted polycyclic fused aromatic group, or a substituted or unsubstituted heterocyclic group having a 5 to 15 carbon atoms; n represents an integer of 1 or 2; and m represents 0.

$R_1$ described above represents a hydrogen atom or a linear chain or branched alkyl group having 1 to 8 carbon atom(s), more preferably having 1 to 4 carbon atom(s). Specified examples can be preferably exemplified, for example, by hydrogen atom, methyl group, ethyl group, propyl group, butyl group, pentyl group, hexyl group, heptyl group, and octyl group. More preferably, it is possible to appropriately exemplify hydrogen atom, methyl group, and ethyl group.

$R_3$ described above represents a substituted or unsubstituted aromatic group, a substituted or unsubstituted polycyclic fused aromatic group, or a substituted or unsubstituted heterocyclic group having a 5 to 15 carbon atoms. As for the substituent, it is possible to preferably exemplify, for example, an alkyl group having 1 to 6 carbon atom(s), more preferably having 1 to 4 carbon atom(s), an alkoxy group having an alkyl chain having 1 to 6 carbon atom(s), more preferably having 1 to 4 carbon atom(s), an alkylamino group having an alkyl chain(s) having 1 to 6 carbon atom(s), more preferably having 1 to 4 carbon atom(s), a halogen atom, a halogenated alkyl group (preferably having an alkyl chain having 1 to 4 carbon atom(s)), a hydroxy group, and an amino group.

In relation to the group represented by $R_3$, specified examples can be preferably exemplified, for example, by pyridyl group, methylpyridyl group, ethylpyridyl group, propylpyridyl group, methoxypyridyl group, ethoxypyridyl group, propyloxypyridyl group, hydroxypyridyl group, aminopyridyl group, N-methylaminopyridyl group, N-ethylaminopyridyl group, N,N,-dimethyleminopyridyl group, N,N,-diethylaminopyridyl group, chloropyridyl group, fluoropyridyl group, difluoropyridyl group, trifluoromethylpyridyl group, phenyl group, methylphenyl group, ethylphenyl group, propylphenyl group, methoxyphenyl group, ethoxyphenyl group, propyloxyphenyl group, hydroxyphenyl group, aminophenyl group, N-methylaminophenyl group, N-ethylaminophenyl group, N,N,-dimethylaminophenyl group, N,N-diethylaminophenyl group, chlorophenyl group, fluorophenyl group, difluorophenyl group, trifluoromethylphenyl group, naphthyl group, methylnaphthyl group, ethylnaphthyl group, propylnaphthyl group, methoxynaphthyl group, ethoxynaphthyl group, propyloxynaphthyl group, hydroxynaphthyl group, aminonaphthyl group, N-methylaminonaphthyl group, N-ethylaminonaphthyl group, N,N-dimethylaminonaphthyl group, N,N-diethylaminonaphthyl group, chloronaphthyl group, fluoronaphthyl group, difluoronaphthyl group, trifluoromethylnaphthyl group, biphenyl group, methylbiphenyl group, ethylbiphenyl group, methoxybiphenyl group, and ethoxybiphenyl group. More preferably, it is possible to appropriately exemplify pyridyl group, phenyl group, methylphenyl group, ethylphenyl group, methoxyphenyl group, ethoxyphenyl group, fluorophenyl group, trifluoromethylphenyl group, naphthyl group, and biphenyl group.

The number of the substituent on the aromatic group, the polycyclic fused aromatic group, or the heterocyclic group can be preferably exemplified by 0 to 3, and the number is more preferably 0 or 1. One or more of the substituent(s) as described above can exist independently respectively as the substituent(s) on the aliphatic hydrocarbon group, the aromatic group, the polycyclic fused aromatic group, or the heterocyclic group.

As described above, n represents an integer of 1 or 2, and m represents 0.

The compounds defined in <3> described above, which are not included in the compounds defined in <4> described above, are specifically exemplified. It is possible to preferably exemplify N-(benzoyl)homocysteic acid, N-(p-toluoyl)homocysteic acid (Compound 6), N-(ethylbenzoyl)homocysteic acid, N-(propylbenzoyl)homocysteic acid, N-(butylbenzoyl)homocysteic acid, N-(methoxybenzoyl)homocysteic acid, N-(ethoxybenzoyl)homocysteic acid, N-(propyloxybenzoyl)homocysteic acid, N-(butyloxybenzoyl)homocysteic acid, N-(hydroxybenzoyl)homocysteic acid, N-(aminobenzoyl)homocysteic acid, N—(N'-methylaminobenzoyl)homocysteic acid, N—(N'-ethylaminobenzoyl)homocysteic acid, N—(N',N'-dimethylaminobenzoyl)homocysteic acid, N—(N',N'-diethylaminobenzoyl)homocysteic acid, N-(chlorobenzoyl)homocysteic acid, N-(fluorobenzoyl)homocysteic acid, N-(difluorobenzoyl)homocysteic acid, N-(trifluoromethylbenzoyl)homocysteic acid, [N-(benzoyl)homocysteic acid]ethyl ester, [N-(toluoyl)homocysteic acid]ethyl ester, [N-(ethylbenzoyl)homocysteic acid]ethyl ester, [N-(propylbenzoyl)homocysteic acid]ethyl ester, [N-(butylbenzoyl)homocysteic acid]ethyl ester, [N-(methoxybenzoyl)homocysteic acid]ethyl ester, [N-(ethoxybenzoyl)homocysteic acid] ethyl ester, [N-(propyloxybenzoyl)homocysteic acid]ethyl ester, [N-(butyloxybenzoyl)homocysteic acid]ethyl ester, [N-(hydroxybenzoyl)homocysteic acid]ethyl ester, [N-(aminobenzoyl)homocysteic acid]ethyl ester, [N—(N'-methylaminobenzoyl)homocysteic acid]ethyl ester, [N—(N'-ethylaminobenzoyl)homocysteic acid]ethyl ester, [N—(N',N'-dimethylaminobenzoyl)homocysteic acid]ethyl ester, [N—(N',N'-diethylaminobenzoyl)homocysteic acid]ethyl ester, [N-(chlorobenzoyl)homocysteic acid]ethyl ester, [N-(fluorobenzoyl)homocysteic acid]ethyl ester, [N-(difluorobenzoyl)homocysteic acid]ethyl ester, [N-(trifluoromethylbenzoyl)homocysteic acid]ethyl ester, N-(naphthoyl)homocysteic acid, N-(methylnaphthoyl)homocysteic acid, N-(ethylnaphthoyl)homocysteic acid, N-(propylnaphthoyl)

homocysteic acid, N-(butylnaphthoyl)homocysteic acid, N-(methoxynaphthoyl)homocysteic acid, N-(ethoxynaphthoyl)homocysteic acid, N-(propyloxynaphthoyl)homocysteic acid, N-(butyloxynaphthoyl)homocysteic acid, N-(hydroxynaphthoyl)homocysteic acid, N-(aminonaphthoyl)homocysteic acid, N—(N'-methylaminonaphthoyl)homocysteic acid, N—(N'-ethylaminonaphthoyl)homocysteic acid, N—(N',N'-dimethylaminonaphthoyl)homocysteic acid, N—(N',N'-diethylaminonaphthoyl)homocysteic acid, N-(chloronaphthoyl)homocysteic acid, N-(fluoronaphthoyl)homocysteic acid, N-(difluoronaphthoyl)homocysteic acid, N-(trifluoromethylnaphthoyl)homocysteic acid, [N-(naphthoyl)homocysteic acid]ethyl ester, [N-(methylnaphthoyl)homocysteic acid]ethyl ester, [N-(ethylnaphthoyl)homocysteic acid]ethyl ester, [N-(propylnaphthoyl)homocysteic acid]ethyl ester, [N-(butylnaphthoyl)homocysteic acid]ethyl ester, [N-(methoxynaphthoyl)homocysteic acid]ethyl ester, [N-(ethoxynaphthoyl)homocysteic acid]ethyl ester, [N-(propyloxynaphthoyl)homocysteic acid]ethyl ester, [N-(butyloxynaphthoyl)homocysteic acid]ethyl ester, [N-(hydroxynaphthoyl)homocysteic acid]ethyl ester, [N-(aminonaphthoyl)homocysteic acid]ethyl ester, [N—(N'-methylaminonaphthoyl)homocysteic acid]ethyl ester, [N—(N'-ethylaminonaphthoyl)homocysteic acid]ethyl ester, [N—(N',N'-dimethylaminonaphthoyl)homocysteic acid]ethyl ester, [N—(N',N'-diethylaminonaphthoyl)homocysteic acid]ethyl ester, [N-(chloronaphthoyl)homocysteic acid]ethyl ester, [N-(fluoronaphthoyl)homocysteic acid]ethyl ester, [N-(difluoronaphthoyl)homocysteic acid]ethyl ester, [N-(trifluoromethylnaphthoyl)homocysteic acid]ethyl ester, N-(biphenylcarbonyl)homocysteic acid, N-(methylbiphenylcarbonyl)homocysteic acid, N-(ethylbiphenylcarbonyl)homocysteic acid, N-(propylbiphenylcarbonyl)homocysteic acid, N-(butylbiphenylcarbonyl)homocysteic acid, N-(methoxybiphenylcarbonyl)homocysteic acid, N-(ethoxybiphenylcarbonyl)homocysteic acid, N-(propyloxybiphenylcarbonyl)homocysteic acid, N-(butyloxybiphenylcarbonyl)homocysteic acid, N-(hydroxybiphenylcarbonyl)homocysteic acid, N-(aminobiphenylcarbonyl)homocysteic acid, N—(N'-methylaminobiphenylcarbonyl)homocysteic acid, N—(N'-ethylaminobiphenylcarbonyl)homocysteic acid, N—(N',N'-dimethylaminobiphenylcarbonyl)homocysteic acid, N—(N',N'-diethylaminobiphenylcarbonyl)homocysteic acid, N-(chlorobiphenylcarbonyl)homocysteic acid, N-(fluorobiphenylcarbonyl)homocysteic acid, N-(difluorobiphenylcarbonyl)homocysteic acid, N-(trifluoromethylbiphenylcarbonyl)homocysteic acid, [N-(biphenylcarbonyl)homocysteic acid]ethyl ester, [N-(methylbiphenylcarbonyl)homocysteic acid]ethyl ester, [N-(ethylbiphenylcarbonyl)homocysteic acid]ethyl ester, [N-(propylbiphenylcarbonyl)homocysteic acid]ethyl ester, [N-(butylbiphenylcarbonyl)homocysteic acid]ethyl ester, [N-(methoxybiphenylcarbonyl)homocysteic acid]ethyl ester, [N-(ethoxybiphenylcarbonyl)homocysteic acid]ethyl ester, [N-(propyloxybiphenylcarbonyl)homocysteic acid]ethyl ester, [N-(butyloxybiphenylcarbonyl)homocysteic acid]ethyl ester, [N-(hydroxybiphenylcarbonyl)homocysteic acid]ethyl ester, [N-(aminobiphenylcarbonyl)homocysteic acid]ethyl ester, [N—(N'-methylaminobiphenylcarbonyl)homocysteic acid]ethyl ester, [N—(N'-ethylaminobiphenylcarbonyl)homocysteic acid]ethyl ester, [N—(N',N'-dimethylaminobiphenylcarbonyl)homocysteic acid]ethyl ester, [N—(N',N'-diethylaminobiphenylcarbonyl)homocysteic acid]ethyl ester, [N-(chlorobiphenylcarbonyl)homocysteic acid]ethyl ester, [N-(fluorobiphenylcarbonyl)homocysteic acid]ethyl ester, [N-(difluorobiphenylcarbonyl)homocysteic acid]ethyl ester, [N-(trifluoromethylbiphenylcarbonyl)homocysteic acid]ethyl ester, isomers thereof, and/or pharmacologically acceptable salts thereof. More preferably, it is possible to appropriately exemplify N-(o-toluoyl)homocysteic acid, N-(m-toluoyl)homocysteic acid, N-(p-toluoyl)homocysteic acid (Compound 6), isomers thereof, and/or pharmacologically acceptable salts thereof.

The compounds as described above have the excellent effect of prophylactic or amelioration for the pigmentation. Further, the compounds are excellent solubility in the hydrophilic or lipophilic solvent, and it is easy to produce the pharmaceutical preparation such as the external preparation for skin or the like. Further, the compounds are excellent skin retention and stability in the preparation, and the compounds exhibit the excellent effect to prevent or ameliorate the pigmentation.

The compound defined in <4> described above will now be described. In the formula, $R_1$ represents a hydrogen atom or a linear chain or branched alkyl group having 1 to 8 carbon atom(s); $R_2$ represents a hydrogen atom; $R_3$ represents a substituted or unsubstituted aromatic group, a substituted or unsubstituted polycyclic fused aromatic group, or a substituted or unsubstituted heterocyclic group having a 5 to 15 carbon atoms; n represents 1; and m represents 0.

$R_1$ described above represents a hydrogen atom or a linear chain or branched alkyl group having 1 to 8 carbon atom(s), more preferably having 1 to 4 carbon atom(s). Specified examples can be preferably exemplified, for example, by hydrogen atom, methyl group, ethyl group, propyl group, butyl group, pentyl group, hexyl group, heptyl group, and octyl group. More preferably, it is possible to appropriately exemplify hydrogen atom, methyl group, and ethyl group.

$R_3$ described above represents a substituted or unsubstituted aromatic group, a substituted or unsubstituted polycyclic fused aromatic group, or a substituted or unsubstituted heterocyclic group having a 5 to 15 carbon atoms. As for the substituent, it is possible to preferably exemplify, for example, an alkyl group having 1 to 6 carbon atom(s), more preferably having 1 to 4 carbon atom(s), an alkoxy group having an alkyl chain having 1 to 6 carbon atom(s), more preferably having 1 to 4 carbon atom(s), an alkylamino group having an alkyl chain(s) having 1 to 6 carbon atom(s), more preferably having 1 to 4 carbon atom(s), a halogen atom, a halogenated alkyl group (preferably having an alkyl chain having 1 to 4 carbon atom(s)), a hydroxy group, and an amino group.

In relation to the group represented by $R_3$, specified examples can be preferably exemplified, for example, by pyridyl group, methylpyridyl group, ethylpyridyl group, propylpyridyl group, methoxypyridyl group, ethoxypyridyl group, propyloxypyridyl group, hydroxypyridyl group, aminopyridyl group, N-methylaminopyridyl group, N-ethylaminopyridyl group, N,N,-dimethyleminopyridyl group, N,N,-diethylaminopyridyl group, chloropyridyl group, fluoropyridyl group, difluoropyridyl group, trifluoromethylpyridyl group, phenyl group, methylphenyl group, ethylphenyl group, propylphenyl group, methoxyphenyl group, ethoxyphenyl group, propyloxyphenyl group, hydroxyphenyl group, aminophenyl group, N-methylaminophenyl group, N-ethylaminophenyl group, N,N,-dimethylaminophenyl group, N,N-diethylaminophenyl group, chlorophenyl group, fluorophenyl group, difluorophenyl group, trifluoromethylphenyl group, naphthyl group, methylnaphthyl group, ethylnaphthyl group, propylnaphthyl group, methoxynaphthyl group, ethoxynaphthyl group, propyloxynaphthyl group, hydroxynaphthyl group, aminonaphthyl group, N-methylaminonaphthyl group, N-ethylaminonaphthyl group, N,N- dimethylaminonaphthyl group, N,N-diethylaminonaphthyl group, chloronaphthyl group, fluoronaphthyl group, difluoronaphthyl group, trifluoromethylnaphthyl group, biphenyl group, methylbiphenyl group, ethylbiphenyl group, methoxybiphenyl group, and ethoxybiphenyl group. More preferably, it is possible to preferably exemplify pyridyl group, phenyl group, methylphenyl group, ethylphenyl group, methoxyphenyl group, ethoxyphenyl group, fluorophenyl group, trifluoromethylphenyl group, naphthyl group, and biphenyl group.

The number of the substituent on the aromatic group, the polycyclic fused aromatic group, or the heterocyclic group can be preferably exemplified by 0 to 3, and the number is more preferably 0 or 1. One or more of the substituent(s) as described above can exist independently respectively as the substituent(s) on the aliphatic hydrocarbon group, the aromatic group, the polycyclic fused aromatic group, or the heterocyclic group.

As described above, n represents 1, and m represents 0.

Specified examples are exemplified in relation to the compounds defined in <4> described above. It is possible to preferably exemplify N-(pyridylcarbonyl)cysteic acid, N-(methylpyridylcarbonyl)cysteic acid, N-(ethylpyridylcarbonyl)cysteic acid, N-(propylpyridylcarbonyl)cysteic acid, N-(methoxypyridylcarbonyl)cysteic acid, N-(ethoxypyridylcarbonyl)cysteic acid, N-(propyloxypyridylcarbonyl)cysteic acid, N-(hydroxypyridylcarbonyl)cysteic acid, N-(aminopyridylcarbonyl)cysteic acid, N—(N'-methylaminopyridylcarbonyl)cysteic acid, N—(N'-ethylaminopyridylcarbonyl)cysteic acid, N—(N',N'-dimethylaminopyridylcarbonyl)cysteic acid, N—(N',N'-diethylaminopyridylcarbonyl)cysteic acid, N-(chloropyridylcarbonyl)cysteic acid, N-(fluoropyridylcarbonyl)cysteic acid, N-(trifluoromethylpyridylcarbonyl)cysteic acid, N-(benzoyl)cysteic acid, N-(o-toluoyl)cysteic acid (Compound 1), N-(m-toluoyl)cysteic acid (Compound 2), N-(p-toluoyl)cysteic acid (Compound 3), N-(ethylbenzoyl)cysteic acid, N-(propylbenzoyl)cysteic acid, N-(butylbenzoyl)cysteic acid, N-(o-methoxybenzoyl)cysteic acid, N-(m-methoxybenzoyl)cysteic acid, N-(p-methoxybenzoyl)cysteic acid (Compound 4), N-(ethoxybenzoyl)cysteic acid, N-(propyloxybenzoyl)cysteic acid, N-(butyloxybenzoyl)cysteic acid, N-(hydroxybenzoyl)cysteic acid, N-(aminobenzoyl)cysteic acid, N—(N'-methylaminobenzoyl)cysteic acid, N—(N'-ethylaminobenzoyl)cysteic acid, N—(N',N'-dimethylaminobenzoyl)cysteic acid, N—(N',N'-diethylaminobenzoyl)cysteic acid, N-(chlorobenzoyl)cysteic acid, N-(fluorobenzoyl)cysteic acid, N-(difluorobenzoyl)cysteic acid, N-(trifluoromethylbenzoyl)cysteic acid, N-(naphthoyl)cysteic acid, N-(methylnaphthoyl)cysteic acid, N-(ethylnaphthoyl)cysteic acid, N-(propylnaphthoyl)cysteic acid, N-(butylnaphthoyl)cysteic acid, N-(methoxynaphthoyl)cysteic acid, N-(ethoxynaphthoyl)cysteic acid, N-(propyloxynaphthoyl)cysteic acid, N-(butyloxynaphthoyl)cysteic acid, N-(hydroxynaphthoyl)cysteic acid, N-(aminonaphthoyl)cysteic acid, N—(N'-methylaminonaphthoyl)cysteic acid, N—(N'-ethylaminonaphthoyl)cysteic acid, N—(N',N'-dimethylaminonaphthoyl)cysteic acid, N—(N',N'-diethylaminonaphthoyl)cysteic acid, N-(chloronaphthoyl)cysteic acid, N-(fluoronaphthoyl)cysteic acid, N-(difluoronaphthoyl)cysteic acid, N-(trifluoromethylnaphthoyl)cysteic acid, N-(biphenylcarbonyl)cysteic acid (Compound 5), N-(methylbiphenylcarbonyl)cysteic acid, N-(ethylbiphenylcarbonyl)cysteic acid, N-(propylbiphenylcarbonyl)cysteic acid, N-(butylbiphenylcarbonyl)cysteic acid, N-(methoxybiphenylcarbonyl)cysteic acid, N-(ethoxybiphenylcarbonyl)cysteic acid, N-(propyloxybiphenylcarbonyl)cysteic acid, N-(butyloxybiphenylcarbonyl)cysteic acid, N-(hydroxybiphenylcarbonyl)cysteic acid, N-(aminobiphenylcarbonyl)cysteic acid, N—(N'-methylaminobiphenylcarbonyl)cysteic acid, N—(N'-ethylaminobiphenylcarbonyl)cysteic acid, N—(N',N'-dimethylaminobiphenylcarbonyl)cysteic acid, N—(N',N'-diethylaminobiphenylcarbonyl)cysteic acid, N-(chlorobiphenylcarbonyl)cysteic acid, N-(fluorobiphenylcarbonyl)cysteic acid, N-(difluorobiphenylcarbonyl)cysteic acid, N-(trifluoromethylbiphenylcarbonyl)cysteic acid, isomers thereof, and/or pharmacologically acceptable salts thereof. More preferably, it is possible to appropriately exemplify N-(o-toluoyl)cysteic acid (Compound 1), N-(m-toluoyl)cysteic acid (Compound 2), N—(P-toluoyl)cysteic acid (Compound 3), N-(o-methoxybenzoyl)cysteic acid, N-(m-methoxybenzoyl)cysteic acid, N-(p-methoxybenzoyl)cysteic acid (Compound 4), N-(2-phenylbenzoyl)cysteic acid, N-(3-phenylbenzoyl)cysteic acid, and N-(4-phenylbenzoyl)cysteic acid (Compound 5).

The compounds as described above have the excellent effect of prophylactic or amelioration for the pigmentation. Further, the compounds are excellent solubility in the hydrophilic or lipophilic solvent, and it is easy to produce the pharmaceutical preparation such as the external preparation for skin or the like. Further, the compounds are excellent skin retention and stability in the preparation, and the compounds exhibit the excellent effect to prevent or ameliorate the pigmentation.

As for the compounds as described above, it is possible to use isomers thereof. The isomer is, for example, a stereoisomer which is, for example, an optical isomer. Further, as for each of the compound represented by the general formula (1) described above and the compounds defined in <2> to <4>, optical isomers of D-isomer and L-isomer exist in addition to a racemic compound (DL-isomers). Any one of the isomers exhibits the excellent effect to prevent or ameliorate the pigmentation. However, it is possible to preferably exemplify L-isomer in view of, for example, the safety for the living body and the stability in the pharmaceutical preparation.

The compound represented by the general formula (1) described above, the compounds defined in <2> to <4>, the isomers thereof, and/or the pharmacologically acceptable salts thereof can be also prepared starting from commercially available cysteic acid, homocysteic acid, and/or their derivatives by deprotective, coupling and protective reactions in according with the following production method described in this specification or the ordinary method described in "Fundamental and Experiments for Peptide synthesis (MARUZEN) et al.

The compounds as described above can be also used as they are as the prophylactic or ameliorating agent for pigmentation. Furthermore, they can be also used as salts after converting them into the form of salt by treating them together with pharmacologically acceptable acid or base. It is possible to preferably exemplify, for example, mineral acid salts including, for example, hydrochloride, sulfate, nitrate, phosphate, and carbonate; organic acid salts including, for example, maleate, fumarate, oxalate, citrate, lactate, tartrate, methanesulfonate, para-toluenesulfonate, and benzenesulfonate; alkali metal salts including, for example, sodium salt and potassium salt; alkaline earth metal salts including, for example, calcium salt and magnesium salt; organic amine salts including, for example, triethylamine salt, triethanolamine salt, ammonium salt, monoethanolamine salt, and piperidine salt; and basic amino acid salts including, for example, lysine salt and alginic acid salt.

The compound represented by the general formula (1), the compounds defined in <2> to <4>, the isomers thereof, and/or the pharmacologically acceptable salts thereof, which are thus obtained as described above, have the excellent prophylactic or ameliorating effect for pigmentation. Therefore, they are useful as the active ingredients of the external preparation for skin. As for the pharmacological action of the active ingredient as described above, it is estimated that their prophylactic or ameliorating activity is caused by the suppression of melanin production through melanocyte activation suppressing activity, for example, the tyrosinase activity inhibiting activity such as the tyrosinase enzyme inhibiting activity, the tyrosinase gene expression suppressing activity, the tyrosinase protein expression suppressing activity, and the tyrosinase-related protein degrading activity.

As shown in Test Examples described later on, the compounds represented by the general formula (1) described above, the compounds defined in <2> to <4> described above, the isomers thereof, and/or the pharmacologically acceptable salts thereof have been confirmed to have the excellent effect to suppress the activation of melanocyte in an in vitro evaluation system. It is considered that the compound represented by the general formula (1) described above, the compounds defined in <2> to <4> described above, the isomers thereof, and/or the pharmacologically acceptable salts thereof exhibit the confirmed effect to suppress the pigmentation in an in vivo evaluation system by suppressing the melanin production on the basis of, for example, the action to suppress the activation of melanocyte as described above. That is, the compound represented by the general formula (1) described above, the compounds defined in <2> to <4> described above, the isomers thereof, and/or the pharmacologically acceptable salts thereof are useful as the active ingredient of the prophylactic or ameliorating agent for pigmentation.

Any compound, which provides any effect other than the prophylactic or ameliorating effect for pigmentation, also exists in the compound represented by the general formula (1) described above, the compounds defined in <2> to <4>, the isomers thereof, and/or the pharmacologically acceptable salts thereof. Any external preparation for skin, which contains the compound in order to express the effect as described above, also belongs to the technical scope of the present invention, because the effect of the present invention is utilized, provided that it is principally aimed to provide the prophylactic or ameliorating effect for pigmentation as the effect of the compound represented by the general formula (1) described above, the compounds defined in <2> to <4>, the isomers thereof, and/or the pharmacologically acceptable salts thereof. The external preparation for skin of the present invention is provided to prevent or ameliorate the pigmentation. The purpose "to prevent or ameliorate the pigmentation" also includes the purpose having any principal object intended to be achieved by preventing or ameliorating the pigmentation, for example, the purpose, for example, for "skin whitening" and "pigmentation spot amelioration".

<External Preparation for Skin of the Present Invention>

The external preparation for skin of the present invention is characterized in that the external preparation for skin contains the prophylactic or ameliorating agent for pigmentation comprising any one of the compound represented by the general formula (1) described above, the compounds defined in <2> to <4>, the isomers thereof, and/or the pharmacologically acceptable salts thereof.

In order to effectively express the prophylactic or ameliorating effect for pigmentation of the compound represented by the general formula (1), the compounds defined in <2> to <4>, the isomers thereof, and/or the pharmacologically acceptable salts thereof, it is preferable to contain one or more of the species selected from the compound represented by the general formula (1), the compounds defined in <2> to <4>, the isomers thereof, and/or the pharmacologically acceptable salts thereof in a total amount of 0.0001% by mass to 20% by mass, more preferably 0.001% by mass to 10% by mass, and much more preferably 0.005 to 5% by mass with respect to the total amount of the external preparation for skin. If the content with respect to the total amount of the external preparation for skin is less than 0.0001% by mass, the prophylactic or ameliorating action for pigmentation is lowered. On the other hand, even if an amount exceeding 20% by mass is used, the effect reaches the plateau. Therefore, it is preferable to adopt the content described above with respect to the total amount of the external preparation for skin.

In the external preparation for skin of the present invention, it is possible to contain any arbitrary component usually used for the cosmetic preparation, other than the essential components as described above. As for the arbitrary component as described above, it is possible to contain, for example, hydrocarbons including, for example, squalane, Vaseline, and microcrystalline wax; esters including, for example jojoba oil, carnauba wax, and octyldodecyl oleate; triglycerides including, for example, olive oil, beef tallow, and coconut oil; fatty acids including, for example, stearic acid, oleic acid, and retinoic acid; higher alcohols including, for example, oleyl alcohol, stearyl alcohol, and octyl dodecanol; anionic surfactants including, for example, sulfosuccinic acid ester and sodium polyoxyethylenealkylsulfate; amphoteric surfactants including, for example, alkyl betaine; cationic surfactants including, for example, dialkylammonium; nonionic surfactants including, for example, sorbitan fatty acid ester, fatty acid monoglyceride, polyoxyethylene adducts thereof, polyoxyethylene alkyl ether, and polyoxyethylene fatty acid ester; polyhydric alcohols including, for example polyethylene glycol, glycerol, and 1,3-butanediol; thickening/gelling agents; antioxidants; ultraviolet absorbing agents; coloring materials; antiseptics; and powders. The external preparation for skin of the present invention can be produced without any difficulty by treating the components as described above in accordance with the ordinary method in addition to the prophylactic or ameliorating agent for pigmentation of the present invention.

The external preparation for skin of the present invention can be produced by treating the essential components and the arbitrary components as described above in accordance with the ordinary method, and processing the components, for example, into a lotion, a milky lotion, an essence, a cream, a pack cosmetic preparation, or a washing preparation. Any form of the external preparation for the skin can be adopted provided that it can be applied to the skin. Because the active ingredient permeates into the skin to express the effect, it is more preferable to use the form of the external preparation which is conformable to skin, such as the lotion, the milky lotion, the cream, the essence et al.

The present invention will be explained in more detail below as exemplified by Examples. However, it goes without saying that the present invention is not limited to only Examples as described below.

EXAMPLES

Production Example 1

Synthesis of L-isomer of Compound 1

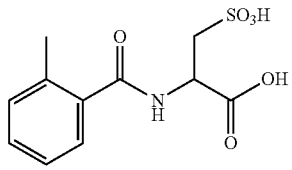 [SMILES: Cc1ccccc1C(=O)NC(CS(=O)(=O)O)C(=O)O]

N-(o-Toluoyl)-L-cysteic acid (L-isomer of Compound 1)

In a recovery flask having a volume of 100 (mL) were placed 3 (g) (17.7 mmol) of L-cysteic acid (Tokyo Chemical Industry Co., Ltd.), tetrahydrofuran 18 (mL) (Wako Pure Chemical Industries, Ltd.), and 18 (mL) of water, and the flask was then cooled in an ice bath. After the cooling was sufficiently performed, potassium carbonate 4.40 (g) (31.6 mmol) (Wako Pure Chemical Industries, Ltd.) was added. o-Toluoyl chloride 3.28 (g) (Tokyo Chemical Industry Co., Ltd.) was successively added so that the temperature of the reaction mixture was not raised. After the addition, the ice bath was removed, and the reaction mixture was stirred at room temperature. The progress of the reaction was confirmed by thin layer chromatography, and then tetrahydrofuran was evaporated under reduced pressure. The obtained residue was washed with ethyl acetate, and then pH was adjusted to be not more than 2 with hydrochloric acid. The filtrate was concentrated, and water (20 ml) was added thereto. The precipitated crystals were obtained by filtration, and the crystals were subjected to the washing with acetone. The filtrated crystals were dried at 60° C. to obtain Compound 1 having the structure described above 0.78 (g) (2.72 mmol). Characteristic values are as follows.

$^1$H-NMR (D$_2$O): δ 2.31 (3H, s), 3.42 (2H, m), 4.86 (1H, m), 7.24 (2H, m), 7.35 (2H, m).

FAB-MS (negative ion mode): M/z=286 ([M−H]$^−$).

Production Example 2

Synthesis of L-isomer of Compound 2

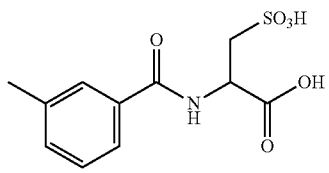

N-(m-Toluoyl)-L-cysteic acid (L-isomer of Compound 2)

In a recovery flask having a volume of 100 (mL) were placed 3 (g) (17.7 mmol) of L-cysteic acid (Tokyo Chemical Industry Co., Ltd.), 18 (mL) of tetrahydrofuran (Wako Pure Chemical Industries, Ltd.), and 18 (mL) of water, and the flask was then cooled in an ice bath. After the cooling was sufficiently performed, potassium carbonate 4.40 (g) (31.6 mmol) (Wako Pure Chemical Industries, Ltd.) and m-toluoyl chloride 2.19 (g) (Tokyo Chemical Industry Co., Ltd.) were successively added so that the temperature of the reaction mixture was not raised. The reaction was performed for 1 hour in the ice bath, and then m-toluoyl chloride 1.09 (g) (Tokyo Chemical Industry Co., Ltd.) was added. After the addition, the ice bath was removed, and the reaction mixture was stirred at room temperature. The progress of the reaction was confirmed by thin layer chromatography, and then tetrahydrofuran was evaporated under reduced pressure. The obtained residue was washed with ethyl acetate, and then pH was adjusted to be not more than 2 with hydrochloric acid. The filtrate was concentrated, and water (18 ml) was added thereto. After performing the aging at 4° C., the precipitated crystals were separated by filtration. The obtained crystals were subjected to the washing with acetone, followed by being filtrated. The filtrated crystals were dried at 60° C. to obtain Compound 2 having the structure described above 1.65 (g) (5.74 mmol). Characteristic values are as follows.

$^1$H-NMR (DMSO-d$_6$): δ 2.36 (3H, s), 2.94 (2H, m), 4.41 (1H, m), 7.36 (2H, d), 7.58 (2H, t), 8.84 (1H, d), 12.5 (1H, bs).

FAB-MS (negative ion mode): M/z=286 ([M−H]$^−$).

Production Example 3

Synthesis of L-isomer of Compound 3

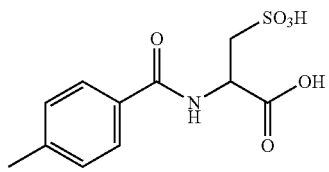

N-(p-Toluoyl)-L-cysteic acid (L-isomer of Compound 3)

In a recovery flask having a volume of 100 (mL) were placed 5 (g) (26.7 mmol) of L-cysteic acid monohydrate (Sigma-Aldrich Co.), 20 (mL) of 1,4-dioxane (Wako Pure Chemical Industries, Ltd.), and 10 (mL) of water, and the flask was then cooled in an ice bath. After the cooling was sufficiently performed, 8 (N) aqueous sodium hydroxide solution 10.7 (mL) and p-toluoyl chloride 3.36 (mL) (Sigma-Aldrich Corporation) were successively added dropwise so that the temperature of the reaction mixture was not raised. After the completion of the dropwise addition, the ice bath was removed, and the reaction mixture was stirred at room temperature. The progress of the reaction was confirmed by thin layer chromatography, and then 1,4-dioxane was evaporated under reduced pressure. The obtained residue was washed with ethyl acetate, and then pH was adjusted to be not more than 2 with hydrochloric acid. The obtained aqueous solution was dried by freeze drying, and the objective substance was extracted with methanol. Methanol was evaporated under reduced pressure, and then the crystallization was performed, followed by being filtrated. The filtrated crystals were dried to obtain Compound 3 having the structure described above 5.79 (g) (20.2 mmol). Characteristic values are as follows.

$^1$H-NMR (D$_2$O): δ 2.32 (3H, s), 3.46 (2H, m), 4.87 (1H, m), 7.25 (2H, d), 7.64 (2H, d).

FAB-MS (negative ion mode): M/z=286 ([M−H]⁻), 308 ([M+Na−H]⁻).

Production Example 4

Synthesis of L-isomer of Compound 4

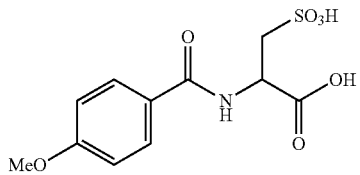

N-(p-Methoxybenzoyl)-L-cysteic acid (L-isomer of Compound 4)

In a recovery flask having a volume of 100 (mL) were placed 2 (g) (11.8 mmol) of L-cysteic acid (Tokyo Chemical Industry Co., Ltd.), 12 (mL) of tetrahydrofuran (Wako Pure Chemical Industries, Ltd.), and 12 (mL) of water, and the flask was then cooled in an ice bath. After the cooling was sufficiently performed, potassium carbonate 2.94 (g) (21.3 mmol) (Wako Pure Chemical Industries, Ltd.) and 4-methoxybenzoyl chloride 1.61 (g) (Tokyo Chemical Industry Co., Ltd.) were successively added so that the temperature of the reaction mixture was not raised. The reaction was performed for 1 hour in the ice bath, and then 4-methoxybenzoyl chloride 0.81 (g) (Tokyo Chemical Industry Co., Ltd.) was added again. After the addition, the ice bath was removed, and the reaction mixture was stirred at room temperature. The progress of the reaction was confirmed by thin layer chromatography, and then tetrahydrofuran was evaporated under reduced pressure. The obtained residue was washed with ethyl acetate, and then pH was adjusted to be not more than 2 with hydrochloric acid. The precipitated crystals were filtrated and washed with water. The filtrate was concentrated, and the reprecipitated crystals were filtrated. The obtained crystals were combined, followed by being subjected to the washing with acetone. The crystals were filtrated, and then the filtrated crystals were dried at 60° C. to obtain Compound 4 having the structure described above 2.47 (g) (8.14 mmol). Characteristic values are as follows.

$^1$H-NMR (D$_2$O): δ 3.45 (2H, m), 3.81 (3H, s), 4.85 (1H, m), 7.00 (2H, d), 7.72 (2H, d).

FAB-MS (negative ion mode): M/z=302 ([M−H]⁻).

Production Example 5

Synthesis of L-isomer of Compound 5

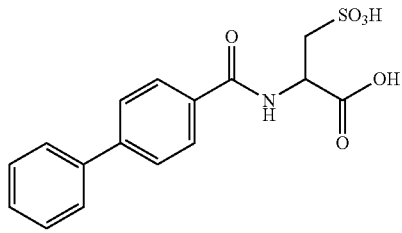

(N-Biphenylcarbonyl)-L-cysteic acid (L-isomer of Compound 5)

In a recovery flask having a volume of 100 (mL) were placed 2 (g) (11.8 mmol) of L-cysteic acid (Tokyo Chemical Industry Co., Ltd.), 12 (mL) of tetrahydrofuran (Wako Pure Chemical Industries, Ltd.), and 12 (mL) of water, and the flask was then cooled in an ice bath. After the cooling was sufficiently performed, potassium carbonate 2.94 (g) (21.3 mmol) (Wako Pure Chemical Industries, Ltd.) and 4-phenylbenzoyl chloride 2.05 (g) (Tokyo Chemical Industry Co., Ltd.) were successively added so that the temperature of the reaction mixture was not raised. The reaction was performed for 1.5 hours in the ice bath, and then 4-phenylbenzoyl chloride 1.02 (g) (Tokyo Chemical Industry Co., Ltd.) was added again. After the addition, the ice bath was removed, and the reaction mixture was stirred at room temperature. The progress of the reaction was confirmed by thin layer chromatography, and then tetrahydrofuran was evaporated under reduced pressure. The obtained residue was washed with ethyl acetate, and then pH was adjusted to be not more than 2 with hydrochloric acid. The precipitated crystals were filtrated and washed with water. The obtained crystals were subjected to the washing with acetone, followed by being filtrated. The filtrated crystals were dried at 60° C. to obtain Compound 5 having the structure described above 2.37 (g) (6.78 mmol). Characteristic values are as follows.

$^1$H-NMR (DMSO-d$_6$): δ 2.96 (2H, m), 4.54 (1H, q), 7.42 (1H, m), 7.51 (2H, m), 7.74 (2H, d), 7.80 (2H, d), 7.90 (2H, d), 8.94 (1H, d).

FAB-MS (negative ion mode): M/z=348 ([M−H]⁻).

Production Example 6

Synthesis of Compound 6

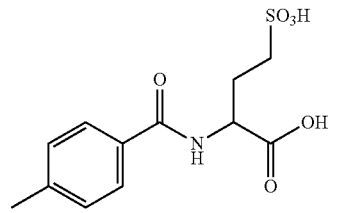

N-(p-Toluoyl)homocysteic acid (Compound 6)

In a recovery flask having a volume of 100 (mL) were placed 2 (g) (10.9 mmol) of DL-homocysteic acid (Sigma-Aldrich Co.), 12 (mL) of tetrahydrofuran (Wako Pure Chemical Industries, Ltd.), and 12 (mL) of water, and the flask was then cooled in an ice bath. After the cooling was sufficiently performed, potassium carbonate 2.71 (g) (19.6 mmol) (Wako Pure Chemical Industries, Ltd.) was added. p-Toluoyl chloride 1.49 (g) (Sigma-Aldrich Corporation) was successively added so that the temperature of the reaction mixture was not raised. The reaction was performed for 1 hour in the ice bath, and then p-toluoyl chloride 0.76 (g) (Sigma-Aldrich Corporation) was added again. After the addition, the ice bath was removed, and the reaction mixture was stirred at room temperature. The progress of the reaction was confirmed by thin layer chromatography, and then tetrahydrofuran was evaporated under reduced pressure. The obtained residue was washed with ethyl acetate, and then pH was adjusted to be not more than 2 with hydrochloric acid. The solution was filtrated, and then the filtrate was concentrated, to which methanol was added. The precipitated crystals were separated by filtration, followed by being subjected to the washing with water. The crystals were filtrated, and the filtrated crystals were dried at 60° C. to obtain Compound 6 having the structure described above 1.95 (g) (6.47 mmol). Characteristic values are as follows.

$^1$H-NMR (DMSO-d$_6$): δ 2.12 (2H, m), 2.35 (3H, s), 2.57 (2H, t), 4.37 (1H, m), 7.26 (2H, d), 7.79 (2H, d), 9.02 (1H, d).

FAB-MS (negative ion mode): M/z=300 ([M−H]$^−$).

Test Example 1

UVB-Induced Cell Activation Inhibition Test Using Normal Human Melanocyte

The inhibitory effect of the compounds on the activation of melanocyte by activating factor produced and released from normal human keratinocyte by the ultraviolet B (UVB) was evaluated by using the index of the cell proliferation of normal human melanocyte.

Normal human keratinocyte (Kurabo Industries, Ltd.) were seeded by Humedia-KG2 medium (Kurabo Industries, Ltd.) at a concentration of 10×10$^4$ cells/well in 24-well plate. Then, cells were cultured for 24 hours.

The compound was dissolved at a concentration of 100 mM in DMSO, which was diluted 1,000 times with Humedia-KG2 medium and used as a sample solution. As for the positive control group, tranexamic acid was dissolved at a concentration of 100 mM in DMSO, which was diluted 1,000 times with Humedia-KG2 medium as a positive control sample solution. As for the negative control group, DMSO was diluted 1,000 times with Humedia-KG2 medium as a negative control sample solution. The concentrations of the compounds were adjusted so that they did not inhibit proliferation of cells.

The medium of normal human keratinocyte was exchanged with Humedia-KG2 medium (sample solution) containing the compound at a predetermined concentration and cells were cultured for further 24 hours. After that, the medium was exchanged with PBS (phosphate buffered saline), and cells were irradiated with the ultraviolet B (UVB) at 5 mJ/cm$^2$ by using an ultraviolet lamp (FL20S•E-30/DMR, Toshiba Medical Supply Co., Ltd.) as a light source. After the ultraviolet radiation, PBS was exchanged with the sample solution. Cells were cultured for further 24 hours, and then the conditioned medium was collected. Normal human melanocyte cells were seeded at the concentration of 3×10$^4$ cells/well in 96-well plate by a medium of Medium 254 (Kurabo Industries, Ltd.). Cells were cultured for 24 hours. After that, the medium was exchanged with the conditioned medium collected from normal human keratinocyte, and cells were cultured for further 24 hours. After 24 hours, the medium was exchanged with Humedia-KG2 medium containing 0.5 mg/mL of 3-(4,5-dimethyl-2-thiazoyl)-2,5-diphenyl-2H-tetrazolium bromide (MTT), and cultured for 3 hour.

The formazan amount was measured by the absorbances at 570 nm and 690 nm of cell lysate lysed with 2-propanol using a microplate reader (Benchmark Plus, Bio-Rad) by subtracting the absorbance at 690 nm from the absorbance at 570 nm.

The inhibitory effect of each compounds on melanocyte proliferation was calculated as the formazan production ratio (%) when the absorbance of negative control group, which was added DMSO and UVB irradiated, was defined as 100%.

It can be evaluated that small production ratio of formazan shows that the melanocyte proliferation is low. Therefore, the small production ratio of formazan means that the inhibitory effect of the compounds is strong against the activation of melanocyte by the melanocyte activating factor released form keratinocyte.

TABLE 1

| Compound | Ultraviolet B (UVB) (mJ/cm$^2$) | Melanocyte proliferation ratio | |
|---|---|---|---|
| | | Average (%) | Standard deviation (%) |
| DMSO | 0 | 48.1 | 3.78 |
| DMSO (negative control) | 5 | 100.0 | 7.08 |
| Tranexamic acid (positive control) | 5 | 80.9 | 8.76 |
| L-Isomer of Compound 1 | 5 | 73.7 | 7.02 |
| L-Isomer of Compound 2 | 5 | 77.0 | 5.72 |
| L-Isomer of Compound 3 | 5 | 58.4 | 8.37 |
| L-Isomer of Compound 4 | 5 | 65.6 | 6.45 |
| L-Isomer of Compound 5 | 5 | 79.0 | 10.38 |
| Compound 6 | 5 | 71.3 | 3.55 |

The melanocyte proliferation ratio shows the mean±S.D. of 3 samples.

Table 1 shows that all these compounds have excellent inhibitory effect, although the inhibitory effect of compounds are different. Therefore, it revealed that all of the compounds have the excellent inhibitory effect to the activation of melanocyte caused by the activating factor produced and released from normal human keratinocyte.

Test Example 2

Ultraviolet Ray-induced Pigmentation Suppression Test Using Guinea Pigs

The hair of the dorsal skin of each of eight pigmented guinea pigs was removed and shaved using an electrical hair clipper and shaver, and each of the sites was covered with a black cloth having a total of four (two on the top and bottom and two on the right and left) irradiation windows with a size of 2×2 cm, and then irradiated with ultraviolet rays of 300 mJ/cm$^2$ using FL20S•E30 lamp as a light source. The operation was repeated on days 1, 3, 5, and 8 after the start of the test to induce pigmentation on the four test sites. Compound 3 was dissolved in ethanol at a concentration of 0.5% (w/v) to prepare samples for application. Further, as a control, ethanol was used alone as a sample for application. On the 1st day of the test after the ultraviolet radiation, the application of samples was started. The respective samples were applied in an amount of 30 μL once a day to the predetermined test sites, and the application was continued for 6 weeks (until day 42 of the test). The skin brightness (L* value) of each of the test sites was measured by a colorimeter (CR-200, Konica Minolta Holdings, Inc.) before the ultraviolet radiation on the day of the start of application (day 1) and after 6 weeks (on the 43rd day of the test), and a ΔL* value was calculated by subtracting an L* value before the ultraviolet radiation from the L* value on 43rd day of the test. Table 2 shows the results. As degree of the pigmentation becomes stronger, the ΔL* value becomes smaller. Therefore, it can be evaluated that, as the ΔL* value becomes larger (high numerical value), pigmentation is more inhibited. The results revealed that compound 3 clearly suppresses the pigmentation induced by the ultraviolet at the concentration of 0.5% when it is applied to the skin.

TABLE 2

| Test sample | Concentration | ΔL* value |
|---|---|---|
| Solvent control group | — | −10.07 ± 0.78 |
| Compound 3 | 0.5% | −8.88 ± 0.54 |

ΔL* value indicates "average ± standard deviation" of 8 animals.

Example 1

Production Example 1 of External Preparation for Skin of the Present Invention A cosmetic (lotion), which was the external preparation for skin of the present invention, was prepared in accordance with a formulation shown in Table 3. That is, the formulation components were heated to 80° C., stirred, dissolved, and cooled by stirring to obtain Lotion 1. In the same way as above, a lotion of Comparative Example 1 was prepared by replacing "compound represented by the general formula (1) of the present invention (Compound 3)" with water.

TABLE 3

| Component | % by weight |
|---|---|
| "Compound represented by the general formula (1) of the present invention (Compound 3)" | 0.5 |
| POE (60) hydrogenated castor oil | 0.1 |
| 1,3-Butanediol | 5.0 |
| Glycerin | 2.0 |
| Polyethylene glycol 400 | 3.0 |
| 1,2-Pentanediol | 3.0 |
| Xanthan gum | 0.1 |
| Potassium hydroxide | 0.05 |
| Methylparaben | 0.2 |
| Water | 86.05 |
| Total | 100 |

Test Example 3

Inhibitory Effect of Cosmetic (Lotion) on Ultraviolet Ray-Induced Pigmentation in Human Inhibitory effects on pigmentation of Compound 3 was investigated by using Lotion 1 and the cosmetic preparation of Comparative Example 1. Two sites each having a size of 1.5 cm×1.5 cm were set at the medial side of the upper arm of each volunteer panelist on the initial day (1st day) of the test. The skin brightness (L* value) of each of the test sites was measured by a colorimeter (CR-300, Konica Minolta Holdings, Inc.). After measuring the skin brightness of the sites on the initial day of the test, the sites were irradiated with ultraviolet rays at twice the minimum erythema dose (2 MED). From the first day after the completion of irradiation, 50 µL of each sample (lotion 1 and comparative example 1) were applied to the test sites predetermined three times a day for 14 consecutive days. 24 hours after the completion of application (on the 15th day), the skin brightness (L* value) of each test site was measured using a colorimeter (CR-300, Konica Minolta Holdings, Inc.), and a ΔL* value was calculated based on an L value of the untreated site. Table 4 shows the results. As degree of the pigmentation becomes stronger, the ΔL* value becomes smaller. Therefore, it can be evaluated that, as the ΔL* value becomes larger (high numerical value), pigmentation is more inhibited. The fact suggests that the lotion 1 which is the external preparation for skin of the present invention has an excellent pigmentation inhibitory effect. This is considered to be provided by the inhibitory effect on melanin production of compound represented by the general formula (1) of the present invention (Compound 3) described above.

TABLE 4

| Test sample | ΔL* value |
|---|---|
| Lotion 1 | −3.25 |
| Comparative Example 1 | −4.02 |

Example 2

Production Example 2 of External Preparation for Skin of the Present Invention A water-in-oil cream was prepared in accordance with a formulation shown in Table 5. Specifically, the components of A and B were heated to 80° C. respectively, and the components of B were gradually added to the components of A, followed by homogenization of emulsified particles by a homogenizer to obtain Cream 1. In the same way as above, a cream of Comparative Example 2 was prepared by replacing "compound represented by the general formula (1) of the present invention (Compound 3)" with water, and a cream of Comparative Example 3 was prepared by replacing "compound represented by the general formula (1) of the present invention (Compound 3)" with arbutin.

TABLE 5

| Component | Parts by weight |
|---|---|
| A | |
| Sucrose fatty acid ester | 0.5 |
| Vaseline | 1.0 |
| Lanolin | 3.0 |
| Liquid paraffin | 8.0 |
| Low viscosity silicone | 30.0 |
| Stearyl alcohol | 0.5 |
| Stearic acid | 0.55 |
| Undecylenic acid monoglyceride | 2.0 |
| Organic modified bentonite | 2.0 |
| B | |
| 1,3-Butanediol | 5.0 |
| Glycerin | 20.0 |
| "Compound represented by the general formula (1) of the present invention (Compound 3)" | 0.5 |
| Methylparaben | 0.2 |
| Water | 26.6 |
| Potassium hydroxide | 0.05 |
| Polyglucosyloxyethyl methacrylate (molecular weight: about 100,000) | 0.1 |
| Total | 100 |

Test Example 4

Inhibitory Effect of Cosmetic (Cream) on Ultraviolet Ray-Induced Pigmentation in Human Inhibitory effects on pigmentation of Cream 1 and the cosmetics of Comparative Example 2 and Comparative Example 3 were examined. Four sites each having a size of 1.5 cm×1.5 cm, which were divided into upper and lower section respectively, were set at the medial side of the upper arm of each of 10 volunteer panelist. The sites were irradiated with ultraviolet rays at a minimum erythema dose (1 MED) once a day for 3 consecutive days, i.e., 3 times. After the third ultraviolet radiation, 50 μL of each sample (Cream 1, comparative example 2 and comparative example 3) were applied to the test sites predetermined three times a day for 28 consecutive days. One site was not treated. After 24 hours after the completion of the application (on the 29th day), the skin brightness (L* value) of each test site was measured using a colorimeter (CR-300, Konica Minolta Holdings, Inc.), and a ΔL* value was calculated based on an L value of the untreated site. As degree of the pigmentation becomes stronger, the L* value becomes smaller. Therefore, it can be evaluated that, as the ΔL* value becomes larger (high numerical value), pigmentation is more inhibited. Table 6 shows the results. The fact suggests that the Cream 1 which is the external preparation for skin of the present invention has an excellent pigmentation inhibitory effect. This is considered to be provided by the inhibitory effect on melanin production of compound represented by the general formula (1) of the present invention (Compound 3) described above.

TABLE 6

| Test sample | ΔL* value |
|---|---|
| Cosmetic preparation (Cream 1) | 0.93 |
| Comparative Example 2 | 0.12 |
| Comparative Example 3 | 0.35 |

INDUSTRIAL APPLICABILITY

The present invention can be applied to the external preparation for skin including, for example, the cosmetic preparation for skin whitening.

What is claimed is:

1. A prophylactic or ameliorating method for pigmentation, comprising applying a compound represented by the following general formula (1), an isomer thereof, and/or a pharmacologically acceptable salt thereof to a subject for which prophylaxis or amelioration for pigmentation is needed in an amount effective to provide prophylaxis or amelioration of pigmentation:

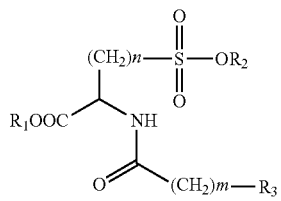

(1)

wherein:
$R_1$ represents a hydrogen atom or a linear chain or branched alkyl group having 1 to 8 carbon atom(s);
$R_2$ represents a hydrogen atom, a substituted or unsubstituted aliphatic hydrocarbon group having 1 to 8 carbon atom(s), a substituted or unsubstituted aromatic group, a substituted or unsubstituted polycyclic fused aromatic group, or a substituted or unsubstituted heterocyclic group having a 5 to 12 carbon atoms;
$R_3$ represents a substituted or unsubstituted aromatic group, a substituted or unsubstituted polycyclic fused aromatic group, or a substituted or unsubstituted heterocyclic group having a 5 to 15 carbon atoms, wherein the substituent of $R_3$ is an alkyl group having 1 to 6 carbon atom(s), an alkoxy group having an alkyl chain having 1 to 6 carbon atom(s), an alkylamino group having an alkyl chain(s) having 1 to 6 carbon atom(s), a halogen atom, a halogenated alkyl group, a hydroxy group, or an amino group;
n represents an integer of 1 or 2, and m represents an integer of 0 to 3.

2. The prophylactic or ameliorating method for pigmentation according to claim 1, wherein in the general formula (1);
$R_1$ represents a hydrogen atom or a linear chain or branched alkyl group having 1 to 8 carbon atom(s);
$R_2$ represents a hydrogen atom;
$R_3$ represents a substituted or unsubstituted aromatic group, a substituted or unsubstituted polycyclic fused aromatic group, or a substituted or unsubstituted heterocyclic group having a 5 to 15 carbon atoms, wherein the substituent of $R_3$ is an alkyl group having 1 to 6 carbon atom(s), an alkoxy group having an alkyl chain having 1 to 6 carbon atom(s), an alkylamino group having an alkyl chain(s) having 1 to 6 carbon atom(s), a halogen atom, a halogenated alkyl group, a hydroxy group, or an amino group;
n represents an integer of 1 or 2, and m represents an integer of 0 to 3.

3. The prophylactic or ameliorating method for pigmentation according to claim 1, wherein in the general formula (1);
$R_1$ represents a hydrogen atom or a linear chain or branched alkyl group having 1 to 8 carbon atom(s);
$R_2$ represents a hydrogen atom;
$R_3$ represents a substituted or unsubstituted aromatic group, a substituted or unsubstituted polycyclic fused aromatic group, or a substituted or unsubstituted heterocyclic group having a 5 to 15 carbon atoms, wherein the substituent of $R_3$ is an alkyl group having 1 to 6 carbon atom(s), an alkoxy group having an alkyl chain having 1 to 6 carbon atom(s), an alkylamino group having an alkyl chain(s) having 1 to 6 carbon atom(s), a halogen atom, a halogenated alkyl group, a hydroxy group, or an amino group;
n represents an integer of 1 or 2, and m represents 0.

4. The prophylactic or ameliorating method for pigmentation according to claim 1, wherein in the general formula (1);
$R_1$ represents a hydrogen atom or a linear chain or branched alkyl group having 1 to 8 carbon atom(s);
$R_2$ represents a hydrogen atom;
$R_3$ represents a substituted or unsubstituted aromatic group, a substituted or unsubstituted polycyclic fused aromatic group, or a substituted or unsubstituted heterocyclic group having a 5 to 15 carbon atoms, wherein the substituent of $R_3$ is an alkyl group having 1 to 6 carbon atom(s), an alkoxy group having an alkyl chain having 1 to 6 carbon atom(s), an alkylamino group having an alkyl chain(s) having 1 to 6 carbon atom(s), a halogen atom, a halogenated alkyl group, a hydroxy group, or an amino group;
n represents 1, and m represents 0.

5. The prophylactic or ameliorating method for pigmentation according to claim 1, wherein the compound represented by the general formula (1) is N-(o-toluoyl)cysteic acid (Compound 1), N-(m-toluoyl)cysteic acid (Compound 2), N-(p-toluoyl)cysteic acid (Compound 3), N-(p-methoxybenzoyl)cysteic acid (Compound 4), N-(4-phenylbenzoyl)cysteic acid (Compound 5), N-(p-toluoyl)homocysteic acid (Compound 6), an isomer thereof, and/or a pharmacologically acceptable salt thereof:

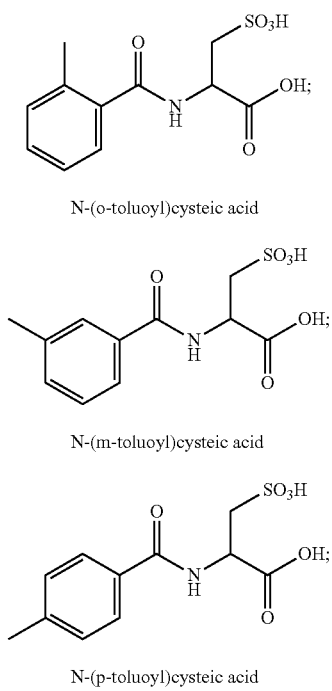

(Compound 1) N-(o-toluoyl)cysteic acid (Compound 2) N-(m-toluoyl)cysteic acid (Compound 3) N-(p-toluoyl)cysteic acid

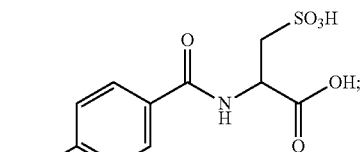

(Compound 4) N-(p-methoxybenzoyl)cysteic acid

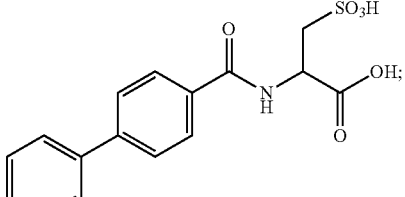

(Compound 5) N-(4-phenylbenzoyl)cysteic acid

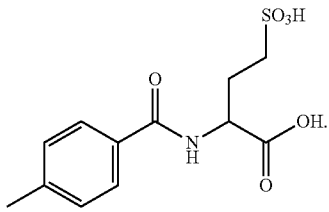

(Compound 6) N-(p-toluoyl)homocysteic acid

* * * * *

UNITED STATES PATENT AND TRADEMARK OFFICE
CERTIFICATE OF CORRECTION

PATENT NO. : 9,066,914 B2  
APPLICATION NO. : 13/521028  
DATED : June 30, 2015  
INVENTOR(S) : Takashi Yamasaki et al.

It is certified that error appears in the above-identified patent and that said Letters Patent is hereby corrected as shown below:

In the Specification

In column 3 at line 23, Change "Cosmetics ," to --Cosmetics,--.

In column 8 at line 2, Change "-dimethyleminopyridyl" to --dimethylaminopyridyl--.

In column 9 at line 38, Change "-dimethyleminopyridyl" to -- -dimethylaminopyridyl--.

In column 11 at line 64, Change "-dimethyleminopyridyl" to -- -dimethylaminopyridyl--.

In column 14 at line 53, Change "-dimethyleminopyridyl" to -- -dimethylaminopyridyl--.

In column 23 at line 54, Change "-thiazoyl)" to -- -thiazolyl)--.

Signed and Sealed this  
Sixteenth Day of February, 2016

Michelle K. Lee  
*Director of the United States Patent and Trademark Office*